US011180734B2

(12) United States Patent
Sabaawy et al.

(10) Patent No.: US 11,180,734 B2
(45) Date of Patent: Nov. 23, 2021

(54) SINGLE CELL-DERIVED ORGANOIDS

(71) Applicant: Rutgers, The State University of New Jersey, New Brunswick, NJ (US)

(72) Inventors: Hatem Sabaawy, Neshanic Station, NJ (US); Monica Bartucci, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 668 days.

(21) Appl. No.: 15/320,496

(22) PCT Filed: Jun. 19, 2015

(86) PCT No.: PCT/US2015/036577
§ 371 (c)(1),
(2) Date: Dec. 20, 2016

(87) PCT Pub. No.: WO2015/196012
PCT Pub. Date: Dec. 23, 2015

(65) Prior Publication Data
US 2017/0198261 A1 Jul. 13, 2017

Related U.S. Application Data

(60) Provisional application No. 62/015,020, filed on Jun. 20, 2014.

(51) Int. Cl.
*C12N 5/09* (2010.01)
*C12N 5/071* (2010.01)
*A01K 67/027* (2006.01)
*G01N 33/50* (2006.01)

(52) U.S. Cl.
CPC ........ *C12N 5/0693* (2013.01); *A01K 67/0278* (2013.01); *C12N 5/0683* (2013.01); *G01N 33/5011* (2013.01); *G01N 33/5082* (2013.01); *A01K 2207/12* (2013.01); *A01K 2207/15* (2013.01); *A01K 2227/105* (2013.01); *A01K 2267/0331* (2013.01); *C12N 2500/25* (2013.01); *C12N 2500/38* (2013.01); *C12N 2500/84* (2013.01); *C12N 2501/11* (2013.01); *C12N 2501/115* (2013.01); *C12N 2501/39* (2013.01); *C12N 2501/395* (2013.01); *C12N 2501/81* (2013.01); *C12N 2502/13* (2013.01); *C12N 2503/02* (2013.01); *C12N 2506/03* (2013.01); *C12N 2513/00* (2013.01)

(58) Field of Classification Search
None
See application file for complete search history.

(56) References Cited

U.S. PATENT DOCUMENTS

| 6,107,540 | A | 8/2000 | Sawyer et al. |
| 8,642,339 | B2 | 2/2014 | Sato et al. |
| 2007/0003541 | A1 | 1/2007 | Faudoa et al. |
| 2010/0330047 | A1 | 12/2010 | Valorani |
| 2014/0165220 | A1 | 6/2014 | Di Santo et al. |

FOREIGN PATENT DOCUMENTS

| EP | 2019858 B1 * | 6/2012 | ........... C12N 5/0607 |
| WO | 2014/082096 A1 | 5/2014 | |

OTHER PUBLICATIONS

Buhler, Patrick, et al. "Primary prostate cancer cultures are models for androgen-independent transit amplifying cells." Oncology reports 23.2 (2010): 465-470. (Year: 2010).*
Zhau, Haiyen E., et al. "Establishment of a three-dimensional human prostate organoid coculture under microgravity-simulated conditions: evaluation of androgen-induced growth and PSA expression." In Vitro Cellular & Developmental Biology—Animal 33.5 (1997): 375-380. (Year: 1997).*
Olumi, Aria F., et al. "Carcinoma-associated fibroblasts direct tumor progression of initiated human prostatic epithelium." Cancer research 59.19 (1999): 5002-5011. (Year: 1999).*
Festuccia, Claudio, et al. "Epithelial and prostatic marker expression in short-term primary cultures of human prostate tissue samples." International journal of oncology 26.5 (2005): 1353-1362. (Year: 2005).*
Calderon-Gierszal, Esther L., and Gail S. Prins. "Directed differentiation of human embryonic stem cells into prostate organoids in vitro and its perturbation by low-dose bisphenol A exposure." PloS one 10.7 (2015). (Year: 2015).*
Devireddy, Laxminarayana R., et al. "A serum-free medium formulation efficiently supports isolation and propagation of canine adipose-derived mesenchymal stem/stromal cells." PloS one 14.2 (2019): e0210250. (Year: 2019).*
Zheng, Xiaoyang, et al. "Proteomic analysis for the assessment of different lots of fetal bovine serum as a raw material for cell culture. Part IV. Application of proteomics to the manufacture of biological drugs." Biotechnology progress 22.5 (2006): 1294-1300. (Year: 2006).*
Wang, Yuzhuo, et al. "Cell differentiation lineage in the prostate." Differentiation 68.4-5 (2001): 270-279 (Year: 2001).*
Chen, et al: "Dissociated Primary Human Prostate Cancer Cells Coinjected with the Immortalized Hs5 Bone Marrow Stromal Cells Generate Undifferentiated Tumors in NOD/SCID-γ Mice", Plos One, Feb. 2013, vol. 8, No. 2, pp. 1-19.
Brakenhielm, et al: "Modulating Metastasis by a Lymphangiogenic Switch in Prostate Cancer", National Institutes of Health, International Journal of Cancer, Nov. 15, 2007, vol. 121, No. 10, pp. 2153-2161.

(Continued)

*Primary Examiner* — Robert J Yamasaki
(74) *Attorney, Agent, or Firm* — Fox Rothschild LLP

(57) ABSTRACT

The present invention relates to organoids derived from a single cell, such as a prostate cancer cell, and methods and compositions relating to the production and use thereof, including cell culture medium for producing organoids and methods of personalized treatment for prostate cancer. The invention further provides a humanized mouse comprising a prostate organoid derived from a patient's prostate cell.

22 Claims, No Drawings

(56) References Cited

OTHER PUBLICATIONS

Goldstein, et al: "Purification and Direct Transformation of Epithelial Progenitor Cells from Primary Human Prostate", National Institutes of Health, Nature Protocols, May 2011, vol. 6, No. 5, pp. 656-667.
Chua, et al: "Single Luminal Epithelial Progenitors can Generate Prostate Organoids in Culture", Nature Cell Biology, Sep. 21, 2014, vol. 16, No. 10, pp. 951-967.
Bartucci et al: "Personalized Medicine Approaches in Prostate Cancer Employing Patient Derived 3D Organoids and Humanized Mice", Frontiers in Cell and Developmental Biology, Jun. 2016, vol. 4, No. 64, pp. 1-8.
International Search Report and Written Opinion dated Sep. 17, 2015 in International Patent Application No. PCT/US2015/036577 (13 pages).

\* cited by examiner

SINGLE CELL-DERIVED ORGANOIDS

CROSS-REFERENCE TO RELATED APPLICATION

This application claims the benefit of U.S. Provisional Application No. 62/015,020 filed Jun. 20, 2014, the disclosure of which is incorporated herein by reference in its entirety.

BACKGROUND OF THE INVENTION

The inability to propagate primary tissues represents a major hurdle to understanding the mechanisms of regeneration and the balance of differentiated cells versus stem cells in adult organisms. A need exists to better understand primary human pathological disorders such as tumor development. For cancer studies, current cancer models do not adequately represent the molecular and cellular diversity of human cancers. Existing human cancer cell lines lack defined and detailed information regarding the clinical presentation of the cancer and have inherent limitations for deciphering the mechanisms of therapy resistance. Therefore, novel methods to maintain primary tissues for cancer and new drug discovery approaches to treat cancer are needed.

Maintaining the balance between normal differentiated cells and progenitor or stem cells is complex. Adult stem cells provide regeneration of different tissues, organs, or neoplastic growth through responding to cues regulating the balance between proliferation, differentiation, and apoptosis. Epigenetic changes, which are independent of the genetic instructions but heritable at each cell division, can be the driving force towards initiation or progression of diseases. Tissue stem cells are heterogeneous in their ability to proliferate, self-renew, and differentiate and they can reversibly switch between different subtypes under stress conditions. Tissue stem cells house multiple subtypes with propensities towards multi-lineage differentiation. Hematopoietic stem cells (HSCs), for example, can reversibly acquire three proliferative states: a dormant state in which the cells are in the quiescent stage of the cell cycle, a homeostatic state in which the cells are occasionally cycling to maintain tissue differentiation, and an activated state in which the cells are cycling continuously. The growth and regeneration of many adult stem cell pools are tightly controlled by these genetic and/or epigenetic responses to regulatory signals from growth factors and cytokines secreted through niche interactions and stromal feedback signals.

Prostate cancer is the most common malignancy and the second most common cause of cancer death in Western men. Despite its prevalence, prostate cancer has proven very difficult to propagate in vitro. Prostate cancer represents a complex organ-like multicellular structure whose survival and function rely upon the dynamic interaction of prostate cancer cells with parenchymal fibroblasts, endothelial cells, immune cells and components of the extracellular matrix (ECM). The lack of prostate cancer models that recapitulate the ECM and cellular diversity of prostate cancer has hampered progress toward understanding disease progression and lackluster therapeutic responses. For example, cell lines grown in monolayers and genetically engineered mouse models fail to mimic the complexities of the prostate cancer microenvironment or reproduce the diverse mechanisms of therapy resistance.

SUMMARY OF THE INVENTION

In one embodiment, the present invention provides a method of making an organoid from a mammalian tissue in vitro comprising: isolating cells from a mammalian tissue to provide isolated cells; culturing the isolated cells in a differentiation medium for a time sufficient to enrich for stem cells and induce differentiation; and amplifying the cells by culturing in an extracellular matrix in an organoid medium for a time sufficient to produce organoids.

In another embodiment, the invention provides an in vitro prostate organoid comprising epithelial cells and mesenchymal cells.

In another embodiment, the invention provides an in vitro prostate organoid derived from primary prostate cancer tissue, wherein the organoid comprises epithelial cells and mesenchymal cells and produces prostatic specific antigen (PSA).

In another embodiment, the invention provides a cell culture medium supplemented with bovine pituitary extract (BPE) and epinephrine.

In another embodiment, the invention provides a cell culture medium supplemented with basic fibroblast growth factor (bFGF), epidermal growth factor (EGF) and hydrocortisone.

In another embodiment, the present invention provides a kit comprising a cell culture medium supplemented with BPE and epinephrine and a cell culture medium supplemented with bFGF, EGF and hydrocortisone.

In another embodiment, the invention provides a method for identifying agents having anticancer activity against prostate cancer cells comprising selecting at least one test agent, contacting a plurality of patient-specific prostate organoids derived from the patient's prostate cancer cell with the test agent, determining the number of prostate organoids in the presence of the test agent and the absence of the test agent, and identifying an agent having anticancer activity if the number of organoids is less in the presence of the agent than in the absence of the agent. In another embodiment, the method provides a step of treating the patient with the agent identified as having anticancer activity against the patient-specific organoids but not against normal organoids.

In another embodiment, the present invention provides immune humanized mice with implanted patient-specific prostate organoids, and methods of using such mice to identify personalized therapies for prostate cancer.

DETAILED DESCRIPTION OF THE INVENTION

In certain embodiments, the present invention provides prostate organoids derived in vitro from normal and cancerous tissues, and methods of making and using such organoids, as well as cell culture media and kits. As disclosed in one embodiment herein, certain growth factors in an in vitro environment containing extracellular matrix molecules in a 3-dimensional culture device may be used to make the organoids.

An organoid is a miniature form of a tissue that is generated in vitro and exhibits endogenous three-dimensional organ architecture. See, e.g., Cantrell and Kuo (2015) *Genome Medicine* 7:32-34. The organoids of the present invention can be used, for example, to: a) determine genomic targets within tumors and prediction of response to therapies in preclinical and clinical trials; b) detect the activity of an anti-cancer agent by examining the number of surviving organoids after treatment; c) detect the activity of a proliferative agent by determining the number of proliferating cells within each organoid and determining gene expression profiling of relevant pathways; d) examine the specificity of agents targeting different cell types within organoids; e) determine the effects of chemotherapy and radiation; f) create mouse models by implantation of the organoid in vivo; g) create preclinical models for examining therapy responses and drug discovery both in vitro and in vivo; and h) determine clonally-targeting anti-cancer therapies.

Accordingly, in one embodiment, the invention provides a method of making an organoid from a mammalian tissue in vitro comprising: isolating cells from a mammalian tissue to provide isolated cells; culturing the isolated cells in a differentiation medium for a time sufficient to enrich for stem cells and induce differentiation; and amplifying the cells by culturing in an extracellular matrix in an organoid medium for a time sufficient to produce organoids. One of ordinary skill in the art can determine a time sufficient to induce differentiation by examining morphological changes associated with differentiation. In one preferred embodiment, the time sufficient to induce differentiation is from about five to about fifteen days. In another preferred embodiment, the time sufficient to induce differentiation is about 14 days. In one preferred embodiment, the time sufficient to produce organoids is from about five to about fifteen days. In another preferred embodiment, the time sufficient to produce organoids is about 14 days.

In one preferred embodiment, the differentiation medium comprises bovine pituitary extract (BPE) and epinephrine. The concentration of BPE present in the differentiation medium may range from about 0.1-100 mg/L. The concentration of epinephrine present in the differentiation medium may range from about 0.1-100 µM. In a further embodiment, the differentiation medium comprises one or more of the following: Insulin (1-10 mg/L), hydrocortisone (0.1-10 µM), gentamicin (5-50 µg/L), amphotericin (1-30 µg/L), transferrin (0.5-25 mg/L), triiodothyronine (0.1-10 µM), epidermal growth factor (EGF) (5-50 ng/mL), and retinoic acid (0.1-10 µM). In a most preferred embodiment, the differentiation medium comprises the following concentrations: Prostate Epithelial Cell Growth Medium (PrEBM™, Lonza) (about 1X); Bovine Pituitary extract (about 52 mg/L); Insulin (about 5 mg/L); Hydrocortisone (about 1 µM); Gentamicin (about 30 µg/L); Amphotericin (about 15 µg/L); Transferrin (about 5 mg/L); Triiodothyronine (about 0.1-10 µM); Epinephrine (about 1X); rhEGF (about 20 ng/mL); Retinoic acid (0.1-10 µM). The differentiation medium may further comprise or be substituted with other supplements, growth factors, antibiotics, vitamins metabolites, and hormones, synthetic or natural with similar properties as known in the art. In a preferred embodiment, the differentiation medium is a commercially available cell culture such as Dulbecco's Modified Eagle Mediun (DMEM; Life Technologies), advanced-DMEM (Life Technologies), or keratinocyte serum free medium (KSFM) (Life Technologies) supplemented with the components described above. In a most preferred embodiment, the differentiation medium is a commercially available prostate epithelial cell growth medium such as PrEBM™ (Lonza) supplemented with the components described above.

In a preferred embodiment, the organoid medium comprises basic fibroblast growth factor (bFGF), epidermal growth factor (EGF) and hydrocortisone. The concentration of bFGF present in the organoid medium may range from about 0.1-10 µM, and the concentration of hydrocortisone present in the organoid medium may range from about 1-50 ng/L. In a further embodiment, the organoid medium may include one or more of the following, BPE (10-100 mg/L), insulin (0.5-25 mg/L), hydrocortisone (0.1-5 µM), gentamicin (5-50 µg/L), amphotericin (1-30 µg/L), transferrin (1-25 mg/L), triiodothyronine (0.1-10 µM), epinephrine (0.1-5X), EGF (1-50 ng/mL), and bFGF (1-50 ng/mL). In a most preferred embodiment, the organoid medium comprises the following concentrations: PrEBM medium (about 1X); Bovine Pituitary extract (about 52 mg/L); Insulin (about 5 mg/L); Hydrocortisone (about 1 µM); Gentamicin (about 30 µµg/L); Amphotericin (about 15 µg/L); Transferrin (about 5 mg/L); Triiodothyronine (0.1-10 µM); Epinephrine (about 1X); rhEGF (about 20 ng/mL); and bFGF (about 20 ng/mL). The following additional 3 components are added every other day (for example 7 times in a 14 day culture period), hydrocortisone (about 1 µM); rhEGF (about 20 ng/mL); and bFGF (about 20 ng/mL). The organoid medium may further comprise or be substituted with other supplements, growth factors, antibiotics, vitamin metabolites, and hormones, synthetic or natural with similar properties as known in the art. In a preferred embodiment, the organoid medium is a commercially available prostate epithelial cell growth medium such as PrEBM™ (Lonza) supplemented with the components described above.

In certain embodiments, the cells are from mammalian cancer tissue, human tissue, human cancer tissue, human prostate tissue, and human primary prostate cancer tissue. In certain embodiments, cells that may be used to make an organoid are human prostate stem cells. Such cells are known in the art and may be identified and isolated using markers, for example, prostate integrin α2β1, CD44, and CD133 (Prominin-1) 10, and CK6a (cytokeratin 6a).

In one embodiment, the cells are positive for at least one marker selected from the group consisting of CD29, CD49b, CD49f, CD44, Erg, and AMACR. In another embodiment, the cells are positive for CD29, CD49b, and CD44. In another embodiment, the cells are positive for CD29, CD49b, CD49f, CD44, Erg, and AMACR. In another embodiment, the cells are positive for Erg and AMACR. Such cells may be identified and isolated by methods of cell sorting that are known in the art. For example, in one embodiment, the cells may be sorted using the SmartFlare™ probe protocol (EMO Millipore).

In one preferred embodiment, the cells are obtained from surgically excised tissues by subjecting the tissues to mechanical dissociation, collagenase treatment, and filtration.

By performing the methods described and inducing differentiation to enrich for stem cells, then reversing the process to induce epigenetic activation of stem cell pathways through response of transcription factors regulating stem cell maintenance, stem cell derived organoids can be maintained for extended periods of time in culture conditions. In certain embodiments, the differentiation step comprises culturing the cells for about 14 days. In a preferred embodiment, the differentiation medium is changed after seven days. In a preferred embodiment of the method, the amplification step is performed under hypoxic conditions, as known in the art. In some embodiments, the amplification step comprises culturing the isolated cells for about 14 days. In certain embodiments, the organoid medium is changed every other day.

In certain embodiments, the prostate cancer cells are co-cultured with stromal cells.

In certain embodiments, the prostate cancer cells are co-cultured with endothelial cells.

In certain embodiments the method is performed with a commercially available extracellular matrix such as Matrigel™. Other extracellular matrices are known in the art for culturing cells. In general, an extracellular matrix comprises laminin, entactin, and collagen. In a preferred embodiment the method is performed using a 3-dimensional culture device (chamber) that mimics an in vivo environment for the culturing of the cells, where preferably the extracellular matrix is formed inside a plate that is capable of inducing the proliferation of stem cells under hypoxic conditions. Such 3-dimensional devices are known in the art. An example of such a device is disclosed by Bansal, N., et al. (2014) *Prostate* 74, 187-200, the disclosure of which is incorporated herein by reference in its entirety. It has been discovered in accordance with the present invention that the use of a 3-dimensional culture device in a method of making organoids has surprising advantages over other formats, as shown in Table 1.

TABLE 1

Advantages and disadvantages of tested formats

| Format | Consistency of Organoids | Reproducibility | Efficiency |
| --- | --- | --- | --- |
| In Matrigel ™ chamber | +++ | +++ | +++ |
| On Matrigel ™ | + | --- | ++ |
| Hanging Drop plates | --- | --- | --- |
| Non adherent plate | + | --- | + |

In another aspect, the invention provides a prostate organoid. The prostate is a hormonally regulated glandular organ with accelerated growth at sexual maturity due to androgen effects on both stromal and epithelial cells. The human prostate is a ductal-acinar gland that is divided into three anatomical zones: peripheral, transitional, and central zones, which are surrounded by a dense and continuous fibromuscular stroma. Human prostate basal cells constitute a continuous layer and form tight junctions between each other. At the histological level, the human prostate contains mainly two types of cells that are called epithelial and stromal cells. The prostate organoids of the present invention resemble the structures of the primary tissue. Upon histological and immunofluorescence analyses, one of skill in the art can determine that the organoids are formed of an inner layer of epithelial cells that may express the epithelial marker E-cadherin and the high molecular weight cytokeratins and that may secrete PSA. The outside layer of the organoid is made of cells of a mesenchymal lineage that may express vimentin, and are surrounded by a thick basement membrane, a feature characteristic of prostatic tissue.

In another aspect, the invention provides a prostate organoid derived in vitro from primary prostate cancer tissue. The most frequent prostate cancer is acinar adenocarcinoma. Tumor heterogeneity can be efficiently modeled using the methods described to make an organoid, by mapping the diagnostic dominant clone and tumor subclones from each patient biopsy sample, generating organoids derived from each clone and defining the genetic signature of each clone. A prostate organoid derived from primary prostate cancer tissue will generally possess secretory function and produce prostatic specific antigen (PSA); express specific phenotype markers resembling the main cellular populations of the prostate gland (i.e. basal, luminal and stromal cells), be serially propogatable for more than six months, and maintain the genetic profiles and characteristic fusion sequences of the original primary tissue.

In another aspect, the invention provides a prostate organoid derived in vitro from surgically excised tissues of tumors identified to express histopathological tissue specific and tumorigenic markers. Single cells from these tissues may be isolated with non-contact laser capture microdissection or by RNA sorting, for example using SmartFlare™ probes to generate single cell organoids with known expression features.

In another embodiment, the invention provides a method for identifying agents having anticancer activity against prostate cancer cells comprising selecting at least one test agent, contacting a plurality of patient-specific prostate organoids derived from the patient's prostate cancer cell with the test agent, determining the number of prostate organoids in the presence of the test agent and the absence of the test agent, and identifying an agent having anticancer activity if the number of organoids is less in the presence of the agent than in the absence of the agent. In another embodiment, the method provides a step of treating the patient with the agent identified as having anticancer activity against the patient-specific organoids.

In another embodiment, the invention provides a method of selecting a personalized treatment for prostate cancer in a subject comprising: selecting at least one form of treatment, contacting a plurality of prostate organoids with the form of treatment, wherein the organoids are derived from prostate cancer cells from the subject, determining the number of prostate organoids in the presence of the treatment and the absence of the treatment, and selecting the treatment if the number of prostate organoids is less in the presence of the treatment than in the absence of the treatment. Various types of therapy can then be examined using the organoids to determine therapy resistance before initiation, to tailor the therapy for each individual patient based on oncogenic driver expression in the organoids, as well as further study induced clonal selection processes that are the frequent causes of relapse. Various forms, combinations, and types of treatment are known in the art, such as radiation, hormone, chemotherapy, biologic, and bisphosphonate therapy. The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject. Terms such as "treating" or "treatment" or "to treat" or "alleviating" or "to alleviate" refer to therapeutic measures that cure, slow down, lessen symptoms of, and/or halt progression of a diagnosed pathologic condition.

The foregoing methods may be facilitated by comparing therapeutic effects in organoids derived from cancer cells and normal cells from the same patient. For example, normal organoids and cancer organoids derived from cells of the same patient can be assessed to determine genetic and epigenetic mutations and gene expression profiles that are cancer-specific, thereby allowing the determination of gene-drug associations and optimization of treatment. Such comparisons also allow one to predict a therapeutic response and to personalize treatment in a specific patient, In another aspect of this method, clonally targeted therapies can be determined by testing the effect of a therapeutic agent on multiple organoids derived from multiple different clones of prostate cancer cells identified in the tumor tissue from a patient, and comparing to the effect of the therapeutic agent on organoids derived from normal cells of the same patient.

In another aspect, the invention provides a cell culture medium supplemented with BPE and epinephrine. In another embodiment, the invention provides a cell culture medium supplemented with bFGF, EGF and hydrocortisone. In a preferred embodiment, the medium is a commercially available prostate epithelial cell growth medium such as PrEBM™ (Lonza).

In another aspect, the invention provides kits to make an organoid from a single cell. In an embodiment, a kit contains containers for a differentiation medium and an organoid medium as previously described. The containers may also contain the necessary supplements (growth factors, antibiotics, hormones, vitamins, amino acids, and combinations thereof) for a differentiation medium and an organoid medium. The kit may further comprise the necessary components for a 3-dimensional culture device, for example, plates, and/or materials for an extracellular matrix, e.g. Matrigel™. The kit may further contain a set of instructions to perform the methods of making an organoid from a single cell as previously described.

In another embodiment, the present invention provides mouse with an implanted patient-specific prostate organoid. In one embodiment, the mouse is a humanized mouse. In another embodiment, the mouse is a human immune system (HIS)—reconstituted mouse. In another embodiment, the mouse is non-obese diabetic (NOD)-Rag (-)-γ chain (-) (NRG) mouse.

Methods of making HIS-reconstituted mice are known in the art and disclosed for example by Drake et al. (2012) *Cell Mol Immunol* 9:215-24 and Harris et al. (2013) *Clinical and Experimental Immunology* 174:402-413. In accordance with one aspect of the present invention, human stem cells from patient, for example from a diagnostic bone marrow sample or HLA-matched, are transplanted into neonatal NRG mice to engraft components of the patient's immune system. The mice are later subjected to grafting with prostate organoids derived from prostate cells of the same patient orthotopically into the prostate. The mice are useful for identifying new treatments, assessing responses to therapy, and evaluating combination therapies.

The following non-limiting examples serve to further illustrate the invention.

EXAMPLE 1

Organoids comprising epithelial and mesenchymal tissues were made from single primary prostate cancer cells. A Matrigel™ chamber with hypoxic conditions was used as well as growth factors that promote self-renewal and factors that induce differentiation simultaneously for 1-2 weeks in a first step to enrich for the stem cell population and induce differentiation. The concentration of the growth factor and point of time of that the growth factor was added determined the cell commitment to self-renewal or cell differentiation programs. The second step involved additional growth factors that promote self-renewal. Within 14 days of the second step culture, organoid structures that were derived from single cells were formed from more than 14 patient derived samples.

Specifically, surgically excised tissues were subjected to mechanical dissociation, collagenase treatment, filtered, and then propagated in a differentiation medium for 1-2 weeks. Following the "differentiating period", cells were collected, washed, and singularly placed in a Matrigel™ chamber; the size of the chamber was determined according to cell densities. The organoid medium with growth factors and cytokines was replaced every other day by aspirating the upper part of the medium from the chamber without disturbing the cellular structures. Within 2 weeks, organoids derived from primary prostate tissue, normal and cancer tissues were formed. These organoids contained multiple cell types including epithelial and mesenchymal tissues.

The differentiation medium used included the following commercially available components and final concentrations: PrEBM medium (1X); Bovine Pituitary extract (52 mg/L); Insulin (5 mg/L); Hydrocortisone (1 μM); Gentamicin (30 μg/L); Amphotericin (15 μg/L); Transferrin (5 mg/L); Triiodothyronine (1X); Epinephrine (1X); rhEGF (20 ng/mL); Retinoic acid (0.1-10 μM). The differentiation media with these components were changed biweekly.

In the next step/second step, the cells were cultured in organoid medium for 14 days with the following components and concentrations: PrEBM medium (1X); Bovine Pituitary extract (52 mg/L); Insulin (5 mg/L); Hydrocortisone (1 μM); Gentamicin (30 μg/L); Amphotericin (15 μg/L); Transferrin (5 mg/L); Triiodothyronine (1X); Epinephrine (1X); rhEGF (20 ng/mL); and bFGF (20 ng/mL). The following additional 3 components were added every other day (7 times in the 14 day culture period), hydrocortisone (1 μM); rhEGF (20 ng/mL); and bFGF (20 ng/mL). Organoid medium with these components were changed every other day, reflecting higher concentrations of growth factors with organoids based on the respective life span of the activity of these growth factors.

EXAMPLE 2

Prostate cancer tissues were isolated from prostatectomy specimens under Institutional Review Board-approved protocols. Deidentified tissues were obtained within 15 minutes of surgery, dissociated and utilized to make organoids using the conditions described in Example 1 hereinabove in 3D droplet chambers of Matrigel™ that mimic the basal lamina of the normal prostate. This process generated multiple prostate organoids that survived for several months and could be rederived to regenerate serial organoids. The conditions described in Example 1 hereinabove were used to derive organoids from 21 out of 24 attempted prostate cancer samples with an efficiency of ~87%. Tissues were from high-risk prostate cancer utilizing prostatectomy tissues or lymph node biopsies and normal adjacent tissue (NAT) cells.

To demonstrate that organoids were clonally derived from single stem cells rather than the result of cell aggregation, patient-derived prostate cancer cells were lentivirally engineered to express enhanced green fluorescence protein (EGFP) and sorted in 3D plates as single cells. Single-cell derived organoids formed after 4 days and completed a well-formed self-organized organoid after 14 days. The percentage of organoid forming capacity varied by 2-3 fold among samples, and was higher in tumoral vs. NAT from the same patients.

The prostate cancer organoids formed rounded well-defined multicellular structures, surrounded by a thick basement membrane, as in the adult prostates. In contrast to spheres from cells from VCaP cell lines, organoids derived from single primary cells showed conserved features of their corresponding primary tissue, such as the expression of E-Cad in inner epithelial cells, VIMENTIN in outer mesenchymal cells, and having a surrounding membrane, as in the mirrorimage biopsy. A sensitive Q-PCR assay to was developed to detect an androgen receptor (AR) signature from single organoids. AR expression and AR variants/targets were modulated by culture conditions within 24 hours.

Attempts by others to develop metastatic prostate cancer organoids have resulted in low efficiency production of organoids comprised solely of epithelial cells, but not primary prostate cancer organoids. Karthaus et al. (2014) *Cell* 159:163-75; Gao et al. (2014) *Cell* 159:176-87.

In contrast, the foregoing examples demonstrate the generation of single stem cell-derived benign prostatic hyperplasia and naive prostate cancer into 3D organoids comprised of both epithelial and mesenchymal tissues.

EXAMPLE 3

The following study was performed to determine whether stromal cell co-culture would enhance the cell growth, migration and invasion of prostate cancer cells grown as 3D organoids, as compared to single tumor cell 3D cultures. Epithelial and stromal cells were labeled with distinct lentiviruses expressing luciferase and fluorescent reporters. The effects of monolayer co-culture of EGFP-labeled prostate cancer cells with normal bone marrow-derived stromal cells labeled with mCherry on the morphology, migration, and proliferation of tumor cells were examined. In parallel, the effects of 3D co-culture of labeled prostate cancer organoids, derived from tumor initiating cells, with bone marrow-derived stromal cells labeled with mCherry were examined on the same parameters examined for monolayer culture. Cell viability assays indicated that proliferation and cell survival increased by ~3 fold with 3D co-culture when compared to monoculture controls, indicating that 3D cells are more responsive to environmental signals.

EXAMPLE 4

Using cells infected with a GFP-Luc lentivirus, organoids from the foregoing examples were implanted in mouse prostates and monitored by bioluminescent imaging (BLI) upon injecting luciferin (150 mg/kg) in living mice using an IVIS® (Perkin Elmer) in vivo imaging system.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein by reference in their entireties.

We claim:

1. A prostate organoid clonally derived in vitro from a single stem cell from primary prostate cancer tissue, wherein the organoid comprises epithelial cells and an outer layer of cells of a mesenchymal lineage surrounded by a basement membrane.

2. A method for identifying an agent having anticancer activity against prostate cancer cells comprising selecting at least one test agent, contacting a plurality of prostate cancer organoids according to claim 1 with the test agent, determining the number of prostate cancer organoids in the presence of the test agent and the absence of the test agent, and identifying an agent having anticancer activity if the number of prostate cancer organoids is less in the presence of the agent than in the absence of the agent.

3. A method of personalized treatment for prostate cancer in a subject comprising: selecting at least one form of treatment, contacting a plurality of prostate cancer organoids according to claim 1 with the form of treatment, wherein the prostate cancer organoids are derived from prostate cancer cells from the subject, determining the number of prostate cancer organoids in the presence of the treatment and the absence of the treatment, and selecting the treatment if the number of prostate cancer organoids is less in the presence of the treatment than in the absence of the treatment.

4. The method of claim 3 further comprising treating the subject with the selected treatment.

5. A humanized mouse engrafted with components of a patient's immune system and comprising a prostate cancer organoid according to claim 1, wherein the prostate cancer organoid is derived from the patient's prostate cancer cell.

6. A prostate organoid clonally derived from a single stem cell made by the method of: isolating cells from a human prostate tissue to provide isolated cells; culturing the isolated cells for a time sufficient to enrich for stem cells; and amplifying a single stem cell by culturing in a three-dimensional culture comprising an extracellular matrix in an organoid medium for a time sufficient to produce at least one organoid, wherein the organoid medium comprises basic fibroblast growth factor (bFGF), epidermal growth factor (EGF) and hydrocortisone,
the at least one organoid clonally derived from the single stem cell and comprising epithelial cells and an outer layer of cells of a mesenchymal lineage surrounded by a basement membrane.

7. The prostate organoid of claim 6, wherein the prostate organoid is derived in vitro from primary prostate cancer tissue.

8. The prostate organoid of claim 7, wherein the prostate organoid produces prostatic specific antigen.

9. A method of making the organoid of claim 6 comprising:
isolating cells from a human prostate tissue to provide isolated cells;
culturing the isolated cells in an enrichment medium for a time sufficient to enrich for stem cells; and
amplifying a single stem cell by culturing in a three-dimensional culture comprising an extracellular matrix in an organoid medium for a time sufficient to produce the organoid, wherein the organoid medium comprises basic fibroblast growth factor (bFGF), epidermal growth factor (EGF) and hydrocortisone,
and wherein the organoid is clonally derived from the single stem cell and comprises epithelial cells and an outer layer of cells of a mesenchymal lineage surrounded by a basement membrane.

10. The method of claim 9 wherein the human prostate tissue is primary prostate cancer tissue.

11. The method of claim 9 wherein the stem cell is amplified under hypoxic conditions.

12. The method of claim 9 wherein the time sufficient to enrich for stem cells is about fourteen days.

13. The method of claim 12 wherein the enrichment medium is changed after seven days.

14. The method of claim 9 wherein the time sufficient to produce the organoid is about five to about fifteen days.

15. The method of claim 9 wherein the organoid medium is changed every other day.

16. The method of claim 9 wherein the bFGF is present at a concentration of about 1-50 ng/L, the EGF is present at a concentration of about 1-50 ng/L, and the hydrocortisone is present at a concentration of about 0.1-10 µM.

17. The method of claim 9 wherein the isolated cells are sorted for the presence of at least one marker selected from the group consisting of CD29, CD49b, CD49f, CD44, Erg, and AMACR.

18. The method of claim 9 wherein the time sufficient to enrich for stem cells is about 5 to about 15 days.

19. The method of claim 9 wherein the enrichment medium comprises retinoic acid, bovine pituitary extract (BPE) and epinephrine.

20. The method of claim 19 wherein the BPE is present at a concentration of about 1-100 mg/L and the retinoic acid is present at a concentration of about 0.1-10 µM.

21. The method of claim 9 wherein the enrichment medium comprises one or more of insulin, hydrocortisone, gentamicin, amphotericin, transferrin, triiodothyronine, epidermal growth factor (EGF), and retinoic acid.

22. The method of claim 9 wherein the organoid medium comprises one or more of BPE, insulin, gentamicin, amphotericin, transferrin, triiodothyronine, and epinephrine.

* * * * *